(12) United States Patent
Li et al.

(10) Patent No.: US 11,951,461 B2
(45) Date of Patent: Apr. 9, 2024

(54) SOLID ACID CATALYST, PREPARATION THEREFOR AND USE THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Yongxiang Li, Beijing (CN); Xuhong Mu, Beijing (CN); Chengxi Zhang, Beijing (CN); Hexin Hu, Beijing (CN); Qiang Fu, Beijing (CN); Xingtian Shu, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 356 days.

(21) Appl. No.: 17/310,180

(22) PCT Filed: Jan. 20, 2020

(86) PCT No.: PCT/CN2020/073171
§ 371 (c)(1),
(2) Date: Jul. 23, 2021

(87) PCT Pub. No.: WO2020/151646
PCT Pub. Date: Jul. 30, 2020

(65) Prior Publication Data
US 2022/0088580 A1  Mar. 24, 2022

(30) Foreign Application Priority Data

Jan. 25, 2019 (CN) .......................... 201910071973.7
Jan. 25, 2019 (CN) .......................... 201910071987.9
Jan. 25, 2019 (CN) .......................... 201910072245.8

(51) Int. Cl.
B01J 29/12  (2006.01)
B01J 35/02  (2006.01)
(Continued)

(52) U.S. Cl.
CPC .......... *B01J 29/126* (2013.01); *B01J 35/023* (2013.01); *B01J 35/1009* (2013.01);
(Continued)

(58) Field of Classification Search
CPC ........ B01J 29/12; B01J 29/126; B01J 35/023; B01J 35/026; B01J 35/10; B01J 35/1009;
(Continued)

(56) References Cited

U.S. PATENT DOCUMENTS 5,863,419 A  1/1999 Huff, Jr. et al.
5,986,158 A  11/1999 Van Broekhoven et al.
(Continued)

FOREIGN PATENT DOCUMENTS

CN  1238747 A  12/1999
CN  1431932 A  7/2003
(Continued)

*Primary Examiner* — In Suk C Bullock
*Assistant Examiner* — Jason Y Chong
(74) *Attorney, Agent, or Firm* — NKL Law; Allen Xue

(57) ABSTRACT

A solid acid catalyst has a macropore specific volume of about 0.30-0.50 ml/g, a ratio of macropore specific volume to specific length of catalyst particles of about 1.0-2.5 ml/(g·mm), and a ratio of specific surface area to length of catalyst particles of about 3.40-4.50 m²/mm. The macropore refers to pores having a diameter of more than 50 nm. An alkylation catalyst is based on the solid acid catalyst and can be used in alkylation reactions. The solid acid catalyst and alkylation catalyst show an improved catalyst service life (Continued)

and/or trimethylpentane selectivity when used in the alkylation of isoparaffins with olefins.

21 Claims, 1 Drawing Sheet

(51) Int. Cl.
*B01J 35/10* (2006.01)
*B01J 37/00* (2006.01)
*B01J 37/04* (2006.01)
*B01J 37/08* (2006.01)
*C07C 2/58* (2006.01)

(52) U.S. Cl.
CPC ....... *B01J 35/1014* (2013.01); *B01J 35/1019* (2013.01); *B01J 35/1023* (2013.01); *B01J 35/1038* (2013.01); *B01J 37/0009* (2013.01); *B01J 37/04* (2013.01); *B01J 37/082* (2013.01); *C07C 2/58* (2013.01); *C07C 2529/12* (2013.01)

(58) Field of Classification Search
CPC ............... B01J 35/1014; B01J 35/1019; B01J 35/1023; B01J 35/1038; B01J 37/0009; B01J 37/04; B01J 37/06; B01J 37/082; B01J 23/34; B01J 23/42; B01J 23/44; B01J 23/462; B01J 23/755; C07C 2/58; C07C 2/62; C07C 2529/12; C07C 2523/34; C07C 2523/42; C07C 2523/44; C07C 2523/46; C07C 2523/755

See application file for complete search history.

(56) References Cited

U.S. PATENT DOCUMENTS

| | | | | |
|---|---|---|---|---|
| 2011/0313227 A1* | 12/2011 | Van Broekhoven | ..... | B01J 23/42 502/355 |
| 2017/0204806 A1 | 7/2017 | Friesth | | |

FOREIGN PATENT DOCUMENTS

| | | |
|---|---|---|
| CN | 1569778 A | 1/2005 |
| CN | 102464539 A | 5/2012 |
| CN | 103964994 A | 8/2014 |
| CN | 105170195 A | 12/2015 |
| CN | 106311317 A | 1/2017 |
| CN | 106631656 A | 5/2017 |
| CN | 107382646 A | 11/2017 |
| CN | 108067286 A | 5/2018 |
| DE | 2354558 C2 | 8/1985 |
| EP | 0216938 A1 | 4/1987 |
| EP | 1286769 B1 | 9/2004 |
| EP | 1392627 B1 | 8/2009 |
| EP | 1527035 B1 | 3/2015 |
| JP | 2003534898 A | 11/2003 |
| JP | 2007522140 A | 8/2007 |
| JP | 2012518522 A | 8/2012 |
| RU | 2190465 C2 | 10/2002 |
| WO | 0191901 A1 | 12/2001 |
| WO | WO-0191901 A1 * | 12/2001 ............ B01J 29/126 |

\* cited by examiner

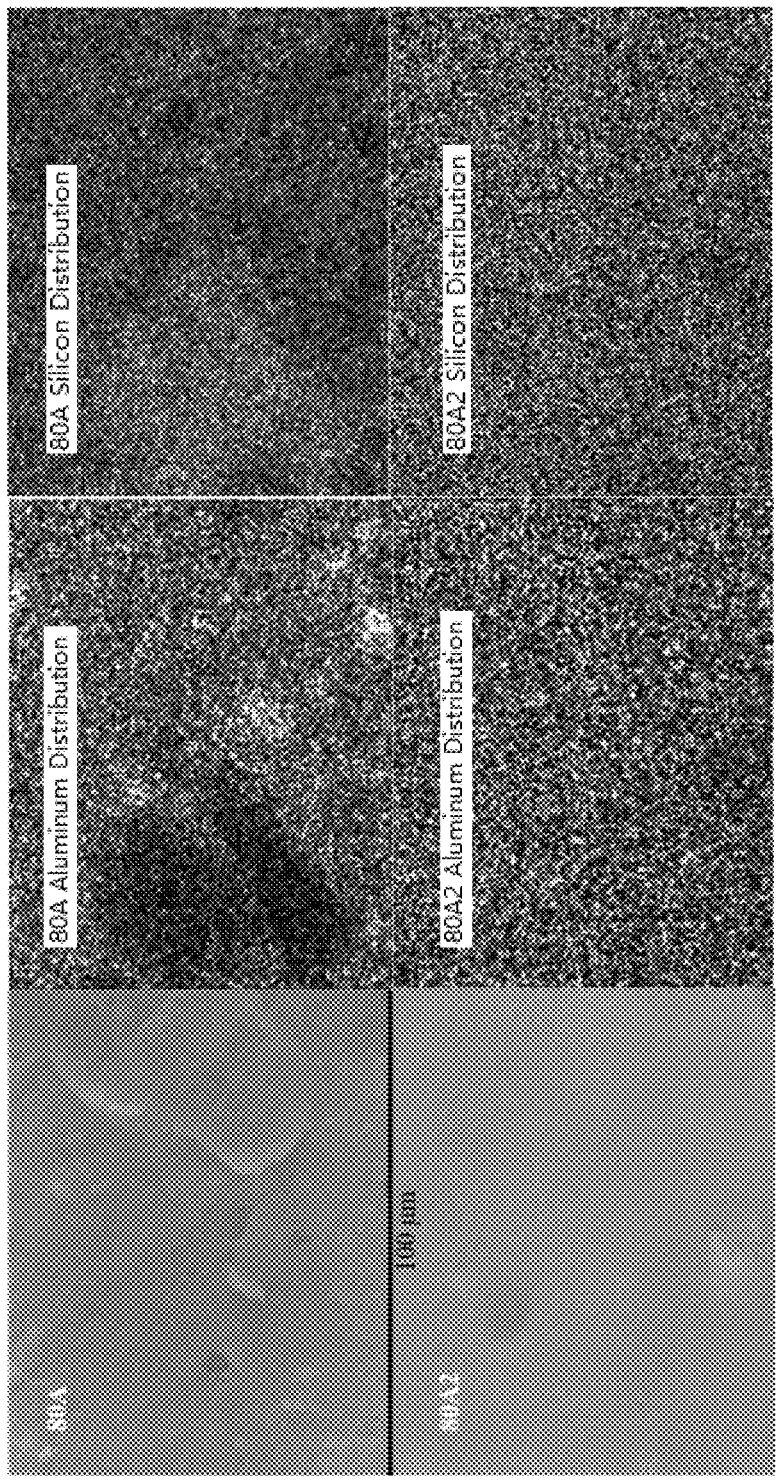

SOLID ACID CATALYST, PREPARATION THEREFOR AND USE THEREOF

CROSS-REFERENCE TO RELATED APPLICATIONS

The present application is a U.S. national stage entry of International Application No. PCT/CN2020/073171, filed Jan. 20, 2020, which claims the priority of Chinese patent application No. 201910072245.8 filed on Jan. 25, 2019, titled "a solid acid catalyst"; Chinese patent application No. 201910071973.7 filed on Jan. 25, 2019, titled "a method for preparing a solid acid catalyst"; and Chinese patent application No. 201910071987.9 filed on Jan. 25, 2019, titled "an alkylation catalyst and use thereof", the contents of which are incorporated herein by reference in their entirety.

TECHNICAL FIELD

The present application relates to the field of solid acid catalysts, particularly to a solid acid catalyst useful in an alkylation process, its preparation and use thereof.

BACKGROUND ART

The synthesis of alkylated gasoline from $C_4$-$C_6$ isoparaffins and $C_3$-$C_6$ olefins through alkylation is an important process in the petroleum refining industry. The alkylated gasoline produced by the process has low vapor pressure, low sensitivity, good antiknock performance, no aromatic hydrocarbon and olefin, and low sulfur content, and is an ideal blending component for clean and high-octane gasoline.

The alkylation reaction is an acid-catalyzed reaction. Currently, the alkylation processes used in industry include liquid acid processes, including sulfuric acid process and hydrofluoric acid process, which use liquid acid (sulfuric acid or hydrofluoric acid) as catalyst to synthesize alkylated gasoline. Due to the corrosivity and toxicity of sulfuric acid and hydrofluoric acid and the hazard to environment caused by the discharge of waste acid during the process, manufacturers are under increasing pressure on safety and environmental protection.

To address these problems, many large oil companies and research institutions worldwide have been devoted to research and development of solid acid alkylation process technologies in an attempt to replace the liquid acid process with an environmentally friendly solid acid process.

The core of the development of solid acid alkylation process is the development of a solid acid catalyst with excellent performance. Solid acid catalyst has the advantages of good stability, no corrosion to equipment, convenient separation from products, little environmental pollution, high relative safety during transportation and the like, and is an ideal form of future catalyst. Solid acid alkylation catalysts are mainly classified into four types: metal halides, solid superacids, supported heteropolyacids and molecular sieves. Although the development of solid acid catalysts for the alkylation of isobutane with butene has been around for decades, the industrialization process of this process technology has been affected by the problem of the rapid deactivation of the solid acid catalyst.

U.S. Pat. No. 5,986,158 discloses an alkylation process using a catalyst comprising a hydrogenation functional component and a solid acid component, which can be regenerated by saturated hydrocarbon washing and hydrogenation. The reaction is carried out in a fixed bed reactor, the active period of the catalyst is only 4-10 hours, and the catalyst has to be regenerated repeatedly. As can be seen in the working examples, the Research Octane Number (RON) of the alkylated gasolines is 91.2, the ratio of trimethylpentane/dimethylhexane is 2.9, $C_5$-$C_7$, $C_8$, $C_{9+}$ are 30.4%, 58.2%, 11.4%, respectively.

EP1527035B1 discloses a continuous alkylation process which is carried out in an apparatus comprising in Zone A at least two reactors connected in series and loaded with a catalyst, and in zone B at least two reactors connected in series and loaded with a catalyst;

each zone cycling back and forth between an alkylation mode and a mild regeneration mode, each zone having at least two reactors in series, the alkylate product stream may or may not be subjected to a preliminary batch separation in which a portion of the alkylate is withdrawn; the catalyst is treated in a mild regeneration mode which comprises contacting the catalyst with hydrogen and a portion of the effluent containing the alkylate produced in the alkylation mode in each of the at least two reactors in the zone.

EP1392627B1 discloses a process for the catalytic alkylation of hydrocarbons, which comprises the steps of (i) reacting an alkylatable compound with an alkylating agent over a solid acid alkylation catalyst to produce an alkylate and (ii) regenerating said catalyst under mild regeneration conditions in the presence of hydrogen and a hydrocarbon, wherein the hydrocarbon comprises at least a portion of the alkylate that has been formed.

CN103964994A discloses an alkylation process, which is characterized in that the alkylation reaction of isobutane and butene is carried out in the presence of a catalyst under alkylation conditions, wherein the catalyst is prepared by a method comprising a step of modifying a molecular sieve and a step of introducing a matrix, the step of modifying the molecular sieve is carried out by uniformly mixing the molecular sieve, one or more substances selected from water, alcohol and ester, and an organic base, treating the mixture in a sealed reaction kettle at a temperature of 100-250° C. under the autogenous pressure, recovering the product obtained after the treatment and subjecting it to ion-exchange with rare earth ion salt.

EP1286769B1 and CN1431932A disclose a catalyst and its use in alkylation, said catalyst comprising catalyst particles comprising a hydrogenation functional component and a solid acid, wherein the ratio of (i) the volume in the pores having a diameter of 40-8000 nm of the catalyst to (ii) the specific length of catalyst particles is 0.01-0.90 ml/(g·mm), and wherein the total pore volume of the catalyst is at least 0.20 ml/g and the volume in the pores having a diameter of 40-8000 nm of the catalyst is below 0.30 ml/g.

However, there remains a need in the art for solid acid catalysts having improved catalytic performance suitable for use in the alkylation of isoparaffins with olefins.

SUMMARY OF THE INVENTION

An object of the present application is to provide a novel solid acid catalyst, its preparation, an alkylation catalyst based on the same, and application thereof in the alkylation of isoparaffins with olefins.

In an aspect, the present application provides a solid acid catalyst having a macropore specific volume in a range of about 0.30-0.50 ml/g, preferably about 0.30-0.40 ml/g, a ratio of macropore specific volume to specific length of catalyst particles in a range of about 1.0-2.5 ml/(g·mm), and a ratio of specific surface area to length of catalyst particles in a range of about 3.40-4.50 m²/mm, wherein the macropore refers to pores having a diameter greater than 50 nm.

In another aspect, there is provided a method for preparing a solid acid catalyst according to the present application, comprising the steps of:

i) providing a slurry comprising a solid acid component;

ii) mixing the slurry comprising the solid acid component with an alumina sol and drying the resulting mixture; and iii) mixing the dried mixture with an extrusion aid and a peptizing agent and shaping, wherein the alumina sol has a particle size in a range of about 20-400 nm.

In yet another aspect, the present application provides a solid acid-based alkylation catalyst, comprising a metal component having a hydrogenation capability, wherein the metal component is present in an amount in a range of about 0.01-10 wt %, calculated as metal and based on the weight of the alkylation catalyst, the alkylation catalyst has a macropore specific volume in a range of about 0.30-0.50 ml/g, preferably about 0.30-0.40 ml/g, a ratio of macropore specific volume to specific length of catalyst particles in a range of about 1.0-2.5 ml/(g·mm), and a ratio of specific surface area to length of catalyst particles in a range of about 3.40-4.50 m²/mm, wherein the macropore refers to pores having a diameter greater than 50 nm.

In yet another aspect, the present application provides an alkylation process comprising a step of subjecting an isoparaffin to an alkylation reaction with an olefin in the presence of a solid acid catalyst and/or an alkylation catalyst according to the present application.

The solid acid catalyst and alkylation catalyst according to the present application have an improved catalyst service life and/or trimethylpentane selectivity when used in alkylation reactions, particularly alkylation reactions for synthesizing alkylated gasoline by using $C_4$-$C_6$ isoparaffins and $C_3$-$C_6$ olefins as starting materials.

BRIEF DESCRIPTION OF THE DRAWINGS

The drawings, forming a part of the present description, are provided to help the understanding of the present application, and should not be considered to be limiting. The present application can be interpreted with reference to the drawings in combination with the detailed description hereinbelow. In the drawings:

FIG. 1 shows a SEM and Energy Dispersive X-Ray Spectroscopy (EDX) mapping of a solid acid catalyst obtained in the working examples, showing morphology and element distribution of the solid acid catalyst obtained.

DETAILED DESCRIPTION OF THE INVENTION

The present application will be further described hereinafter in detail with reference to particular embodiments thereof and the accompanying drawings. It should be noted that the particular embodiments of the present application are provided for illustration purpose only, and are not intended to be limiting in any manner.

Any specific numerical value, including the endpoints of a numerical range, described in the context of the present application is not restricted to the exact value thereof, but should be interpreted to further encompass all values close to said exact value. Moreover, regarding any numerical range described herein, arbitrary combinations can be made between the endpoints of the range, between each endpoint and any specific value within the range, or between any two specific values within the range, to provide one or more new numerical range(s), where said new numerical range(s) should also be deemed to have been specifically described in the present application.

Unless otherwise stated, the terms used herein have the same meaning as commonly understood by the person skilled in the art; and if the terms are defined herein and their definitions are different from the ordinary understanding in the art, the definition provided herein shall prevail.

In the context of the present application, in addition to those matters explicitly stated, any matter or matters not mentioned are considered to be the same as those known in the art without any change. Moreover, any of the embodiments described herein can be freely combined with another one or more embodiments described herein, and the technical solutions or ideas thus obtained are considered as part of the original disclosure or original description of the present application, and should not be considered to be a new matter that has not been disclosed or anticipated herein, unless it is clear to the person skilled in the art that such a combination is obviously unreasonable.

All of the patent and non-patent documents cited herein, including but not limited to textbooks and journal articles, are hereby incorporated by reference in their entireties.

As mentioned above, in a first aspect, the present application provides a solid acid catalyst having a macropore specific volume in a range of about 0.30-0.50 ml/g, preferably about 0.30-0.40 ml/g, a ratio of macropore specific volume to specific length of catalyst particles in a range of about 1.0-2.5 ml/(g·mm), and a ratio of specific surface area to length of catalyst particles in a range of about 3.40-4.50 m²/mm, wherein the macropore refers to pores having a diameter greater than 50 nm.

According to the regulations of International Union of Pure and Applied Chemistry (IUPAC), pores having a diameter of greater than 50 nm are designated as "macropore", and the volume within such pores is designated as "macropore volume".

In this context, macropore specific volume refers to the volume of macropores per unit mass of catalyst particles. The solid acid catalyst according to the present application has a macropore specific volume in a range of about 0.30-0.50 ml/g, preferably about 0.30-0.40 ml/g, more preferably at least about 0.35 ml/g, for example about 0.35-0.40 ml/g.

In this context, the specific length of catalyst particles refers to the ratio of the geometric volume to the geometric surface area of the solid portion of catalyst particles. Methods for determining geometric volume and geometric surface area are well known to the person skilled in the art, and they can be determined, for example, as described in DE2354558, the content of which is hereby incorporated by reference in its entirety. It should be noted that the specific length of catalyst particles is different from the diameter of catalyst particles. For example, for cylindrical catalyst particles, the diameter of the particles is 4-6 times greater than the specific length thereof depending on the diameter and length of the particles, and for spherical catalyst particles, the diameter of the particles is 6 times greater than the specific length thereof. The specific length of catalyst particles of the solid acid catalysts according to the present application is preferably in a range of about 0.15-0.4 mm, more preferably about 0.18-0.36 mm, particularly preferably about 0.20-0.32 mm.

The ratio of macropore specific volume to specific length of catalyst particles of the solid acid catalyst according to the present application is in a range of about 1.0-2.5 ml/(g·mm), preferably about 1.1-1.8 ml/(g·mm).

In this context, the total pore specific volume refers to the total pore volume per unit mass of catalyst particles. The total pore specific volume of the solid acid catalyst according to the present application is at least about 0.40 ml/g, preferably at least about 0.45 ml/g.

The particles of the solid acid catalyst according to the present application may have a variety of different shapes, including spherical, cylindrical, annular, and symmetrical or asymmetrical multi-lobed shapes (e.g., butterfly, trilobal, quadralobal). The average diameter of catalyst particles is preferably at least about 1.0 mm, the upper limit of which is preferably about 5.0 mm. In this context, the diameter of a catalyst particle refers to the longest line segment among line segments connecting any two points on the cross section of the catalyst particle, and can be measured by a conventional measuring means such as a vernier caliper.

In a particular embodiment, the solid acid catalyst according to the present application comprises a solid acid component and a matrix material.

In a preferred embodiment, the solid acid component comprises a molecular sieve. According to the present application, the molecular sieve can be selected from a variety of molecular sieves, for example, can be one or more selected from the group consisting of Y molecular sieves, β molecular sieves, MOR molecular sieves, MCM-22 molecular sieves, and MCM-36 molecular sieves. In some preferred embodiments, the solid acid component comprises a Y molecular sieve having a lattice constant in a range of about 2.430-2.470 nm, preferably about 2.440-2.460 nm, and a silica to alumina molar ratio in a range of about 5-15.

In some alternative embodiments, the solid acid component may comprise a non-zeolitic solid acid, such as a heteropolyacid, silica-alumina, sulfated oxides such as sulfated oxides of zirconium, titanium, or tin, mixed oxides of zirconium, molybdenum, tungsten, phosphorus, or the like, chlorided alumina or clay, or the like.

In a preferred embodiment, the solid acid catalyst according to the present application comprises about 2-98 wt % of the solid acid component and about 2-98 wt % of the matrix material, preferably about 5-95 wt % of the solid acid component and about 5-95 wt % of the matrix material, more preferably about 15-85 wt % of the solid acid component and about 15-85 wt % of the matrix material, for example about 20-80 wt % of the solid acid component and about 20-80 wt % of the matrix material, or about 60-80 wt % of the solid acid component and about 20-40 wt % of the matrix material, based on the total weight of the solid acid component and the matrix material.

In a preferred embodiment, the matrix material comprises alumina, the precursor of which is derived at least in part from an alumina sol having a particle size in a range of about 20-400 nm.

In a preferred embodiment, the specific surface area of the solid acid catalyst according to the present application is not less than about 500 $m^2/g$, more preferably not less than about 550 $m^2/g$. In a preferred embodiment of the solid acid catalyst according to the present application, the solid acid component is highly dispersed in the matrix material at a micron level, wherein the specific surface area of the solid acid component is not less than about 650 $m^2/g$ and the specific surface area of the matrix material is not greater than about 400 $m^2/g$. After the solid acid component is dispersed in the matrix material in a micron level, the specific surface area of catalyst particles per unit length thereof shall fluctuate within a narrow range, while there shall not be a significant change resulted from the large difference between the specific surface area of the solid acid component and the specific surface area of the matrix material.

The ratio of the specific surface area of the solid acid catalyst according to the present application to the length of catalyst particles is in a range of about 3.40-4.50 $m^2/mm$, preferably about 3.90-4.50 $m^2/mm$. The length of catalyst particles is obtained by randomly selecting 1 g of catalyst particles, measuring the length of each particle of the 1 g catalyst particles, and adding the length of each particle together. For spherical particles, the length of each particle is the diameter of the sphere; for stripe-shaped particles (including those having a cross-sectional shape of butterfly, trilobal, quadralobal and other special shapes), the length of each particle is the stripe length of the particle; for annular particles, the length of each particle is the outer diameter of the annulus.

In a second aspect, there is provided a method for preparing a solid acid catalyst, comprising the steps of:
  i) providing a slurry comprising a solid acid component;
  ii) mixing the slurry comprising the solid acid component with an alumina sol and drying the resulting mixture, and
  iii) mixing the dried mixture with an extrusion aid and a peptizing agent and shaping,
wherein the alumina sol has a particle size in a range of about 20-400 nm.

In the method according to the present application, the particle size of the alumina sol used is in a range of about 20-400 nm, preferably about 20-300 nm.

In a preferred embodiment, the solid acid component comprises a molecular sieve. Further preferably, the molecular sieve is one or more selected from the group consisting of Y molecular sieves, β molecular sieves, MCM-22 molecular sieves and MOR molecular sieves. Particularly preferably, the solid acid component comprises a Y molecular sieve having a lattice constant in a range of about 2.430-2.470 nm, preferably about 2.440-2.460 nm.

In some alternative embodiments, the solid acid component may comprise one or more selected from the group consisting of heteropolyacids, silica-aluminas, sulfated oxides, chlorided aluminas, and clays.

In some particular embodiments, the slurry comprising the solid acid component is a slurry of the solid acid component in water. In particular, said step i) may comprise slurrying the solid acid component with water to form said slurry comprising the solid acid component.

In a preferred embodiment, the alumina sol is used in an amount of about 2-98 wt %, preferably about 5-95 wt %, more preferably about 15-85 wt %, even more preferably about 20-80 wt %, and most preferably about 20-40 wt %, based on the total weight of the solid acid component and the alumina sol, calculated as alumina.

The drying of step ii) may be carried out in a manner well known to the person skilled in the art, and there is no strict requirement in the present application. For example, the drying may be carried out at 80-150° C. for 1-10 hours, preferably at 100-120° C. for 3-6 hours.

In the present application, the extrusion aid used may be those well known to the person skilled in the art, for example one or more selected from the group consisting of sesbania powder, oxalic acid, tartaric acid, citric acid, and the like, preferably sesbania powder; the peptizing agent used may also be those well known to the person skilled in the art, for example one or more selected from nitric acid, hydrochloric acid, acetic acid, formic acid, citric acid, trichloroacetic acid and the like, preferably nitric acid.

According to the present application, in step iii), the particles of the solid acid catalyst may be formed into various shapes, including but not limited to spheres, cylinders, annuluses, and symmetric or asymmetric multilobals (e.g., butterflies, trilobes, quadralobes), as long as the resulting solid acid catalyst satisfies the requirement of a macropore specific volume of about 0.30-0.50 ml/g, preferably about 0.30-0.40 ml/g, a ratio of macropore specific volume to specific length of catalyst particles in a range of about 1.0-2.5 ml/(g·mm), and a ratio of specific surface area to length of catalyst particles in a range of about 3.40-4.50 m$^2$/mm, wherein the macropore refers to pores having a diameter of greater than 50 nm. In a preferred embodiment, the resulting solid acid catalyst has the characteristics as described above, which will not be described in detail here again.

In a particular embodiment, the shaping of step iii) may comprise forming the solid acid catalyst into a desired shape, followed by drying and calcining to obtain a shaped solid acid catalyst. The drying and calcining of step iii) may be carried out in a manner well known to the person skilled in the art, and there is no strict requirement in the present application. For example, the drying may be carried out at 80-150° C. for 1-10 hours, preferably at 100-120° C. for 3-6 hours; the calcining may be carried out at 400-800° C. for 1-10 hours, preferably at 500-700° C. for 2-6 hours, and the calcining atmosphere may be air atmosphere.

In a third aspect, the present application provides a solid acid-based alkylation catalyst, comprising a metal component having a hydrogenation capability, wherein the metal component is present in an amount of about 0.01-10 wt %, calculated as metal and based on the weight of the alkylation catalyst, and the alkylation catalyst has a macropore specific volume in a range of about 0.30-0.50 ml/g, preferably about 0.30-0.40 ml/g, more preferably at least about 0.35 ml/g, for example about 0.35-0.40 ml/g; a ratio of macropore specific volume to specific length of catalyst particles in a range of about 1.0-2.5 ml/(g·mm), preferably about 1.1-1.8 ml/(g·mm); a ratio of specific surface area to length of catalyst particles in a range of about 3.40-4.50 m$^2$/mm, preferably about 3.90-4.50 m$^2$/mm, wherein the macropore refers to pores having a diameter of greater than 50 nm.

In a particular embodiment, the alkylation catalyst according to the present application further comprises a solid acid component and a matrix material, the total amount of the solid acid component and the matrix material being in a range of about 90 wt % to about 99.99 wt %, preferably about 99 wt % to about 99.9 wt %, based on the weight of the alkylation catalyst.

In a preferred embodiment, the solid acid component comprises a molecular sieve. According to the present application, the molecular sieve can be selected from a variety of molecular sieves, for example, can be one or more selected from the group consisting of Y molecular sieves, β molecular sieves, MOR molecular sieves, MCM-22 molecular sieves, and MCM-36 molecular sieves. In some preferred embodiments, the solid acid component comprises a Y molecular sieve having a lattice constant in a range of about 2.430-2.470 nm, preferably about 2.440-2.460 nm, and a silica to alumina molar ratio in a range of about 5-15.

In some alternative embodiments, the solid acid component may comprise a non-zeolitic solid acid, such as a heteropolyacid, silica-alumina, sulfated oxides such as sulfated oxides of zirconium, titanium, or tin, mixed oxides of zirconium, molybdenum, tungsten, phosphorus, or the like, chlorided alumina or clay, and the like.

In a preferred embodiment, the alkylation catalyst according to the present application comprises, based on the total weight of the solid acid component and the matrix material, about 2-98 wt % of the solid acid component and about 2-98 wt % of the matrix material, preferably about 5-95 wt % of the solid acid component and about 5-95 wt % of the matrix material, more preferably about 15-85 wt % of the solid acid component and about 15-85 wt % of the matrix material, and for example, may comprise about 20-80 wt % of the solid acid component and about 20-80 wt % of the matrix material, or about 60-80 wt % of the solid acid component and about 20-40 wt % of the matrix material.

In a preferred embodiment, the matrix material comprises alumina, the precursor of which is derived at least in part from an alumina sol having a particle size in a range of about 20-400 nm.

According to the present application, the alkylation catalyst can be an alkylation catalyst comprising or consisting of a solid acid catalyst according to the present application and a metal having a hydrogenation capability supported thereon, wherein the various features described above for the solid acid catalyst are equally applicable to the alkylation catalyst and will not be described in detail herein. In the alkylation catalyst according to the application, the solid acid catalyst constitutes an active component, and the metal having a hydrogenation capability constitutes a regeneration auxiliary component, and after the regeneration auxiliary is loaded on the solid acid catalyst, inactivated solid acid catalyst can be regenerated under appropriate conditions in the presence of hydrogen, so that repeated regeneration and recycling of the catalyst can be realized.

According to the present application, suitable metals having a hydrogenation capability include, but are not limited to, Group VIII metals, preferably Group VIII noble metals. More preferably, one or more of rhodium, palladium and platinum are used as the Group VIII noble metal. The metal having a hydrogenation capability is present in an amount of about 0.01-10 wt %, preferably about 0.1-1 wt %, calculated as metal and based on the weight of the alkylation catalyst.

The alkylation catalyst according to the present application may be obtained by loading the metal having a hydrogenation capability on catalyst particles by a conventional loading method, for example, a typical preparation procedure may comprise loading the metal having a hydrogenation capability on the solid acid catalyst according to the present application by impregnating catalyst particles with a solution containing the metal having a hydrogenation capability and/or by ion exchange; or alternatively, a typical preparation procedure may comprise adding a precursor of the metal having a hydrogenation capability to a liquid mixture comprising a solid acid component and an alumina sol having a particle size in a range of about 20-400 nm, and then drying and shaping the resulting mixture.

In a fourth aspect, the present application provides a method for preparing a solid acid-based alkylation catalyst, comprising the steps of:
i) providing a shaped solid acid catalyst,
ii) loading a metal having a hydrogenation capability onto the solid acid catalyst to obtain a catalyst precursor, and
iii) drying and calcining the catalyst precursor obtained in step ii) to obtain the alkylation catalyst,
wherein the solid acid catalyst has a macropore specific volume in a range of about 0.30-0.50 ml/g, preferably about 0.30-0.40 ml/g, a ratio of macropore specific volume to specific length of catalyst particles in a range of about 1.0-2.5 ml/(g·mm), and a ratio of specific surface area to length of catalyst particles in a range of about 3.40-4.50 m$^2$/mm, wherein the macropore refers to pores having a diameter greater than 50 nm.

In a particular embodiment, the solid acid catalyst of step i) is a solid acid catalyst according to the present application, or a solid acid catalyst obtained by the method for preparing a solid acid catalyst according to the present application.

According to the present application, said step ii) can be carried out by means well known to the skilled person, for example by loading said metal having a hydrogenation capability on said solid acid catalyst by impregnating catalyst particles with a solution comprising the metal having a hydrogenation capability and/or by ion exchange.

According to the present application, the metal having a hydrogenation capability used in step ii) includes, but is not limited to, Group VIII metals, preferably Group VIII noble metals. More preferably, one or more of rhodium, palladium and platinum are used as the Group VIII noble metal. The metal having a hydrogenation capability is used in an amount of about 0.01-10 wt %, preferably about 0.1-1 wt %, calculated as metal and based on the weight of the alkylation catalyst.

The drying and calcining of step iii) may be carried out in a manner well known to the person skilled in the art, and there is no strict requirement in the present application. For example, the drying may be carried out at 80-150° C. for 1-10 hours, preferably at 100-120° C. for 3-6 hours; the calcining may be carried out at 400-800° C. for 1-10 hours, preferably at 400-600° C. for 1-5 hours, and the calcining atmosphere may be an inert atmosphere or an air atmosphere.

In a fifth aspect, the present application provides a method for preparing a solid acid-based alkylation catalyst, comprising the steps of:

i) providing a slurry comprising a solid acid component;

ii) mixing the slurry comprising the solid acid component with an alumina sol and a precursor of a metal having a hydrogenation capability and drying the resulting mixture, and iii) mixing the dried mixture with an extrusion aid and a peptizing agent and shaping, wherein the alumina sol has a particle size in a range of about 20-400 nm.

In this aspect of the present application, the selection of the alumina sol, the solid acid component, the extrusion aid, the peptizing agent, and the like can be the same as those described above for the preparation of the solid acid catalyst according to the present application, and will not be described in detail herein.

In some particular embodiments, the slurry comprising the solid acid component is a slurry of the solid acid component in water. In particular, said step i) may comprise slurrying the solid acid component with water to form said slurry comprising the solid acid component.

The drying of step ii) may be carried out in a manner well known to the person skilled in the art, and there is no strict requirement in the present application. For example, the drying may be carried out at 80-150° C. for 1-10 hours, preferably at 100-120° C. for 3-6 hours.

According to the present application, the precursors of the metal having a hydrogenation capability used in step ii) may be various soluble compounds of said metal, such as soluble salts, wherein said metal having a hydrogenation capability include, but is not limited to, Group VIII metals, preferably Group VIII noble metals. More preferably, one or more of rhodium, palladium and platinum are used as the Group VIII noble metal. The metal having a hydrogenation capability is used in an amount of about 0.01-10 wt %, preferably about 0.1-1 wt %, calculated as metal and based on the weight of the alkylation catalyst.

According to the present application, in step iii) the particles of said alkylation catalyst may be shaped into a variety of different shapes, including but not limited to spherical, cylindrical, annular, and symmetrical or asymmetrical multilobal shapes (e.g. butterfly, trilobal, quadrulobal), as long as the resulting alkylation catalyst satisfies the requirements of a macropore specific volume in a range of about 0.30-0.50 ml/g, preferably about 0.30-0.40 ml/g, a ratio of macropore specific volume to specific length of catalyst particles in a range of about 1.0-2.5 ml/(g·mm), a ratio of specific surface area to specific length of catalyst particles in a range of about 3.40-4.50 m²/mm, wherein the macropore refers to pores having a diameter of greater than 50 nm. In a preferred embodiment, the resulting alkylation catalyst has the features described above and will not be described in detail herein.

In particular embodiments, the shaping of step iii) may comprise forming the alkylation catalyst into a desired shape, followed by drying and calcining to provide a shaped alkylation catalyst. The drying and calcining of step iii) may be carried out in a manner well known to the person skilled in the art, and there is no strict requirement in the present application. For example, the drying may be carried out at 80-150° C. for 1-10 hours, preferably at 100-120° C. for 3-6 hours; the calcining may be carried out at 400-800° C. for 1-10 hours, preferably at 500-700° C. for 2-6 hours, and the calcining atmosphere may be air atmosphere.

In a sixth aspect, the present application provides an alkylation process comprising a step of subjecting an isoparaffin to an alkylation reaction with an olefin in the presence of a solid acid catalyst and/or an alkylation catalyst according to the present application.

Preferably, the isoparaffin is a $C_4$-$C_6$ isoparaffin, and the olefin is a $C_3$-$C_6$ mono-olefin; more preferably, the $C_4$-$C_6$ isoparaffin is isobutane and the $C_3$-$C_6$ mono-olefin is one or more of 1-butene, 2-butene and isobutene.

In a preferred embodiment, the alkylation reaction is carried out under the following conditions: a temperature of about 30-100° C., a pressure of about 1.5-5.0 MPa, a feed rate of about 10-3000 ml/($g_{cat}$·h), and a mole ratio of isoparaffin to olefin of about 6-1000. Further preferably, the alkylation reaction is carried out under the following conditions: a temperature of about 40-100° C., a pressure of about 2.0-5.0 MPa, a feed rate of about 10-2000 ml/($g_{cat}$·h), and a molar ratio of isoparaffin to olefin of about 15-1000.

The alkylation process according to the present application may be performed using various types of reactors including, but not limited to, fluidized bed reactors, slurry bed reactors, and fixed bed reactors. The process may be carried out in a single or multiple reactors.

Compared with solid acid catalysts and alkylation catalysts with similar compositions but with ratio of macropore specific volume to specific length of catalyst particles and/or ratio of specific surface area to length of catalyst particles falling outside the ranges defined herein, the solid acid catalyst and alkylation catalyst with the specific physicochemical parameters provided herein are capable of improving catalyst service life and/or trimethylpentane selectivity and limiting the yield of $C_{9+}$ byproducts when used in alkylation reactions, particularly alkylation reactions for synthesis of alkylated gasolines from $C_4$-$C_6$ isoparaffins and $C_3$-$C_6$ olefins; meanwhile, the alkylation catalyst can be regenerated in the presence of hydrogen, and the activity of the regenerated alkylation catalyst can be restored to the level of a fresh catalyst.

In preferred embodiments, the present application provides the following technical solutions:

Solution A1: a solid acid catalyst characterized in that the solid acid catalyst has a macropore specific volume in a range of about 0.30-0.40 ml/g, a ratio of macropore specific volume to specific length of catalyst particles in a range of about 1.0-2.5 ml/(g·mm), a ratio of specific surface area to particle length in a range of about 3.40-4.50 m$^2$/mm, and wherein the macropore refers to pores having a diameter greater than 50 nm.

Solution A2: the catalyst according to Solution A1, wherein the macropore specific volume is at least about 0.35 ml/g.

Solution A3: the catalyst according to Solution A1, wherein the ratio of macropore specific volume to specific length of catalyst particles is in a range of about 1.1-1.8 ml/(g·mm).

Solution A4: the catalyst according to Solution A1, wherein the specific length of catalyst particles is about 0.15-0.4 mm, preferably about 0.18-0.36 mm, more preferably about 0.20-0.32 mm.

Solution A5: the catalyst according to Solution A1, wherein the total pore specific volume is at least about 0.40 ml/g, preferably at least about 0.45 ml/g.

Solution A6: the catalyst according to Solution A1, wherein the specific surface area is not less than about 500 m$^2$/g.

Solution A7: the catalyst according to Solution A1, wherein the solid acid is a molecular sieve.

Solution A8: the catalyst according to Solution A7, wherein the molecular sieve is one or more selected from the group consisting of Y molecular sieves, β molecular sieves, MCM-22 molecular sieves and MOR molecular sieves.

Solution A9: the catalyst according to Solution A8, wherein the Y molecular sieve has a lattice constant in a range of about 2.430-2.470 nm, preferably about 2.440-2.460 nm.

Solution A10: the catalyst according to Solution A1, further comprising a matrix material of alumina.

Solution A11: the catalyst according to Solution A10, wherein the matrix material is present in an amount of about 2-98 wt %, preferably about 10-70 wt %.

Solution B1: a method for preparing a solid acid catalyst, comprising the steps of mixing a slurry comprising a solid acid component with an alumina sol, drying, mixing with an extrusion aid and a peptizing agent, and shaping, wherein the alumina sol has a particle size in a range of 20-400 nm.

Solution B2: the method according to Solution B 1, wherein the alumina sol has a particle size in a range of about 20-300 nm.

Solution B3: the method according to Solution B1, wherein the solid acid component is a molecular sieve.

Solution B4: the method according to Solution B3, wherein the molecular sieve is one or more selected from the group consisting of Y molecular sieves, β molecular sieves, MCM-22 molecular sieves and MOR molecular sieves.

Solution B5: the method according to Solution B4, wherein the Y molecular sieve has a lattice constant in a range of about 2.430-2.470 nm, preferably about 2.440-2.460 nm.

Solution B6: the method according to Solution B1, wherein the alumina sol is present in an amount of about 2-98 wt %, preferably about 10-70 wt %, calculated as alumina and based on the amount of the solid acid catalyst.

Solution B7: the method according to Solution B1, wherein the extrusion aid is selected from the group consisting of sesbania powder, oxalic acid, tartaric acid, citric acid, preferably sesbania powder.

Solution B8: the method according to Solution B 1, wherein the peptizing agent is selected from nitric acid, hydrochloric acid, acetic acid, formic acid, citric acid or trichloroacetic acid, preferably nitric acid.

Solution B9: the method according to Solution B1, wherein the solid acid component further comprises one or more selected from the group consisting of heteropolyacids, silica-aluminas, sulfated oxides, chlorided alumina and clays.

Solution C1: an alkylation catalyst, comprising about 0.01-10 wt % of a metal component having a hydrogenation capability based on the amount of the alkylation catalyst, said alkylation catalyst having a macropore specific volume in a range of about 0.30-0.40 ml/g, a ratio of macropore specific volume to specific length of catalyst particles in a range of about 1.0-2.5 ml/(g·mm), a ratio of specific surface area to particle length in a range of about 3.40-4.50 m$^2$/mm, wherein said macropore refers to pores having a diameter greater than 50 nm.

Solution C2: the catalyst according to Solution C1, wherein the metal having a hydrogenation capability is a Group VIII metal, preferably a Group VIII noble metal, more preferably one or more of rhodium, palladium, platinum.

Solution C3: the catalyst according to Solution C2, wherein the metal having a hydrogenation capability is present in an amount of about 0.01-10 wt %, preferably about 0.1-1 wt %, calculated as metal and based on the weight of the alkylation catalyst.

Solution C4: the catalyst according to Solution C1, wherein the macropore specific volume is at least about 0.35 ml/g.

Solution C5: the catalyst according to Solution C1, wherein the ratio of macropore specific volume to specific length of catalyst particles is in a range of about 1.1-1.8 ml/(g·mm).

Solution C6: the catalyst according to Solution C1, wherein the specific length of catalyst particles is in a range of about 0.15-0.4 mm, preferably about 0.18-0.36 mm, more preferably about 0.20-0.32 mm.

Solution C7: the catalyst according to Solution C1, wherein the total pore specific volume is at least about 0.40 ml/g, preferably at least about 0.45 ml/g.

Solution C8: the catalyst according to Solution C1, wherein the specific surface area is not less than about 500 m$^2$/g.

Solution C9: the catalyst according to Solution C1, the matrix material is alumina. Solution C10: the catalyst according to Solution C9, wherein the alumina precursor is an alumina sol having a particle size in a range of about 20-400 nm.

Solution C11: the catalyst according to Solution C10, wherein the alumina sol is present in an amount of about 2-98 wt %, preferably about 10-70 wt %, based on the weight of the alumina, of the solid acid catalyst.

Solution C12: the catalyst according to Solution C1, wherein the solid acid acts as an active component.

Solution C13: the catalyst according to Solution C12, wherein the solid acid component is a molecular sieve.

Solution C14: the catalyst according to Solution C13, wherein the molecular sieve is one or more selected from the group consisting of Y molecular sieves, β molecular sieves, MCM-22 molecular sieves and MOR molecular sieves.

Solution C15: the catalyst according to Solution C14, wherein the Y molecular sieve has a lattice constant in a range of about 2.430-2.470 nm, preferably about 2.440-2.460 nm.

Solution C16: the catalyst according to Solution C13, wherein the solid acid component is further selected from the group consisting of heteropolyacids, silica-aluminas, sulfated oxides, chlorided alumina or clays.

Solution C17: the catalyst according to Solution C16, wherein the sulfated oxide is a sulfated oxide of zirconium, titanium or tin.

Solution C18: an alkylation process for the alkylation of an isoparaffin with an olefin, characterized in that an alkylation catalyst according to one of Solutions $C_1$ to $C_{17}$ is used.

Solution C19: the process according to Solution C18, wherein the isoparaffin comprises a $C_4$-$C_6$ isoparaffin, and the olefin is a $C_3$-$C_6$ mono-olefin.

Solution C20: the process according to Solution C19, wherein the $C_4$-$C_6$ isoparaffin is isobutane and the $C_3$-$C_6$ mono-olefin is one or more of 1-butene, 2-butene, and isobutylene.

Solution C21: the process according to Solution C20 wherein the reaction conditions include: a temperature of about 30-100° C., a pressure of about 1.5-5.0 MPa, a feed rate of about 10-3000 ml/($g_{cat}$·h), and a molar ratio of isobutane to butene of about 6-1000; preferred alkylation reaction conditions include: a temperature of about 40-100° C., a pressure of about 2.0-5.0 MPa, a feed rate of about 10-2000 ml/($g_{cat}$·h), and a molar ratio of isobutane to butene of about 15-1000.

EXAMPLES

The present application will be further illustrated by the following examples, but is not limited thereto.

In the following examples and comparative examples, the physicochemical properties of solid acid catalysts and alkylation catalysts were determined as follows.

The measurement of macropore volume and total pore volume was performed by the mercury intrusion method in accordance with the Washburn equation, $$D=(-4\cdot\gamma\cdot\cos\theta)/p$$

wherein D represents the pore size, p represents the pressure applied during the measurement, γ represents the surface tension and was set as 485 dynes/cm, θ represents the contact angle and was set as 130°.

Measurement of average diameter of catalyst particles: the diameter of the particle was measured as the longest side distance of a cross-section of the particle using a vernier caliper, and the average diameter of catalyst particles was calculated as the average value of the diameters of those catalyst particles measured.

Measurement of specific surface area: the specific surface area of the catalyst was measured by adopting the nitrogen low-temperature adsorption method, and the specific surface area was calculated using the BET formula.

Measurement of catalyst particle length: 1 g of catalyst particles was randomly selected, the length of each particle in the 1 g of catalyst particles was measured, and the lengths of the particles were added up to obtain the catalyst particle length; the length of each particle was measured using a vernier caliper.

In the following examples and comparative examples, the technical effect of the alkylation process was evaluated and analyzed as follows:

Quartz sand (20-40 meshes) was weighed, filled into a non-thermostatic section at the lower end of a tubular reactor, and compacted, a three-layer nickel screen was installed, 100 g of an alkylation catalyst was loaded and compacted, another three-layer nickel screen was installed, and quartz sand of 20-40 meshes was filled into a non-thermostatic section at the upper end of the reactor, and compacted. Finally, proper amounts of quartz cotton and nickel screen were filled in sequence.

The reactor was connected to pipelines, after the airtightness and the smoothness of the pipelines were tested, air in the device was purged with nitrogen for three or more times, and then purged with hydrogen for three times. The hydrogen flow was set as 300 mL/min and the back pressure was set as 3.0 MPa, a heating source was turned on, the heating rate was set as 1° C./min, and the reactor was heated to 200° C. and kept for 1 h; and then heated to 450° C. at a rate of 1° C./min and kept for 3 h. After the pretreatment, the alkylation catalyst was cooled to the reaction temperature in the examples, hydrogen in the device was purged with nitrogen for three or more times, and after the purge, a reactant was fed at a certain feed rate and reacted under the reaction conditions described in the examples.

The distribution of the alkylation reaction product was determined by Agilent 7890A gas chromatograph equipped with $Al_2O_3$ and PONA columns and a high pressure sampler. Sample were collected after the back pressure valve and before the vent of the tail gas, and the collection of the sample was carried out once every two hours. The sample was divided into two parts at the injection port, a low boiling point mixture ($C_4$ or lower hydrocarbons) at 0.01-0.1 minutes entered an $Al_2O_3$ column, and high boiling point species ($C_5$ or higher hydrocarbons) at 0.2-9.5 minutes were blown into the PONA column by carrier gas. The chromatogram obtained was identified using a gasoline analysis software (developed by Sinopec Research Institute of Petroleum Processing) and the percentage content of each component was calculated.

The starting materials used in the following examples and comparative examples are as follows:

1. Y molecular sieve (provided by Catalyst Branch of Sinopec), having a specific surface area of 680 m²/g, a pore volume of 0.36 ml/g, a lattice constant of 2.457 nm, and m($SiO_2$/$Al_2O_3$)=9, designated as Ya.

2. Several nano-alumina sols (provided by Catalyst Branch of Sinopec):
   Al-1: having an alumina concentration of 5%, and an average particle size of 20 nm;
   Al-2: having an alumina concentration of 15%, and an average particle size of 150 nm;
   Al-3: having an alumina concentration of 20% and an average particle size of 300 nm.

3. $Al_2O_3$ binder powder (provided by Catalyst Branch of Sinopec): having a specific surface area of 280 m²/g, a pore volume of 0.98 ml/g, and an average particle size of 10 µm.

4. Nitric acid (provided by Sinopharm Chemical Reagent Co., Ltd.): having a purity of 65-68%.

5. Sesbania powder (provided by Catalyst Branch of Sinopec): industrial level.

Examples 1 to 3

These examples illustrate the preparation of a solid acid catalyst according to the present application.

Y molecular sieve Ya was slurried with water to form a molecular sieve slurry with a solid content of 200 kg/m³, alumina sol Al-1 was added into the molecular sieve slurry at a dry weight ratio of Ya to Al-1 of 60:40, 80:20 and 95:5, respectively, stirred for 4 hours to obtain a uniform mixture. After being dried at 110° C. for 4 hours, a powder mixture was obtained, then 3 wt % (based on the dry weight of the molecular sieve and the alumina sol calcined at 600° C.) of nitric acid and sesbania powder was added, and water was added to ensure that the weight ratio of water to powder in the resulting mixture was 0.8. The mixture was uniformly mixed and kneaded, and then extruded into bars. The wet bars obtained were dried at 110° C. for 4 hours, and then calcined at 600° C. for 3 hours to obtain a shaped solid acid catalyst.

The resulting solid acid catalysts were designated as 60A1, 80A1, and 95A1, respectively, of which the properties are shown in Table 1.

Examples 4 to 6

These examples illustrate the preparation of a solid acid catalyst according to the present application.

Y molecular sieve Ya was slurried with water to form a molecular sieve slurry with a solid content of 200 kg/m³, alumina sol Al-2 was added into the molecular sieve slurry at a dry weight ratio of Ya to Al-2 of 60:40, 80:20 and 95:5, respectively, stirred for 4 hours to obtain a uniform mixture. After being dried at 110° C. for 4 hours, a powder mixture was obtained, then 3 wt % (based on the dry weight of the molecular sieve and the alumina sol calcined at 600° C.) of nitric acid and sesbania powder was added and water was added to ensure that the weight ratio of water to powder in the resulting mixture was 0.8. The mixture was uniformly mixed and kneaded, and then extruded into bars. The wet bars obtained were dried at 110° C. for 4 hours, and then calcined at 600° C. for 3 hours to obtain a shaped solid acid catalyst.

The resulting solid acid catalysts were designated as 60A2, 80A2, and 95A2, respectively, of which the properties are shown in Table 1.

Examples 7 to 9

These examples illustrate the preparation of a solid acid catalyst according to the present application.

Y molecular sieve Ya was slurried with water to form a molecular sieve slurry with a solid content of 200 kg/m³, alumina sol Al-3 was added into the molecular sieve slurry at a dry weight ratio of Ya to Al-3 of 60:40, 80:20 and 95:5, respectively, stirred for 4 hours to obtain a uniform mixture. After being dried at 110° C. for 4 hours, a powder mixture was obtained, then 3 wt % (based on the dry weight of the molecular sieve and the alumina sol calcined at 600° C.) of nitric acid and sesbania powder was added, and water was added to ensure that the weight ratio of water to powder in the resulting mixture was 0.8. The mixture was uniformly mixed and kneaded, and then extruded into bars. The wet bars obtained were dried at 110° C. for 4 hours, and then calcined at 600° C. for 3 hours to obtain a shaped solid acid catalyst.

The resulting solid acid catalysts were designated as 60A3, 80A3, and 95A3, respectively, of which the properties are shown in Table 1.

Comparative Example 1

This comparative example illustrates the preparation of a solid acid catalyst not according to the present application.

Y molecular sieve Ya was mixed with an $Al_2O_3$ binder powder at a dry weight ratio of 60:40, then 3 wt % (based on the dry weight of the molecular sieve and the $Al_2O_3$ binder powder calcined at 600° C.) of nitric acid and sesbania powder was added, and water was added to ensure that the weight ratio of water to powder in the resulting mixture was 0.8. The mixture was uniformly mixed and kneaded, and then extruded into bars. The wet bars obtained were dried at 110° C. for 4 hours, and then calcined at 600° C. for 3 hours to obtain a shaped comparative solid acid catalyst.

The comparative solid acid catalyst was designated as 60A, of which the properties are shown in Table 1.

Comparative Example 2

This comparative example illustrates the preparation of a solid acid catalyst not according to the present application.

Y molecular sieve Ya was mixed with an $Al_2O_3$ binder powder at a dry weight ratio of 80:20, then 3 wt % (based on the dry weight of the molecular sieve and the $Al_2O_3$ binder powder calcined at 600° C.) of nitric acid and sesbania powder was added, and water was added to ensure that the weight ratio of water to powder in the resulting mixture was 0.8. The mixture was uniformly mixed and kneaded, and then extruded into bars. The wet bars obtained were dried at 110° C. for 4 hours, and then calcined at 600° C. for 3 hours to obtain a shaped comparative solid acid catalyst.

The comparative solid acid catalyst was designated as 80A, of which the properties are shown in Table 1.

Comparative Example 3

This comparative example illustrates the preparation of a solid acid catalyst not according to the present application.

Y molecular sieve Ya was mixed with an $Al_2O_3$ binder powder at a dry weight ratio of 95:5, then 3 wt % (based on the dry weight of the molecular sieve and the $Al_2O_3$ binder powder calcined at 600° C.) of nitric acid and sesbania powder was added, and water was added to ensure that the weight ratio of water to powder in the resulting mixture was 0.8. The mixture was uniformly mixed and kneaded, and then extruded into bars. The wet bars obtained were dried at 110° C. for 4 hours, and then calcined at 600° C. for 3 hours to obtain a shaped comparative solid acid catalyst.

The comparative solid acid catalyst was designated as 95A, of which the properties are shown in Table 1.

TABLE 1

Properties of solid acid catalysts obtained in Examples 1-9 and Comparative Examples 1-3

| Ex. No. | Catalyst No. | Particle shape of solid acid catalyst | Macropore specific volume ml/g | Specific length of particles mm | Ratio of macropore specific volume to specific length of particles ml/(g · mm) | Total pore specific volume ml/g | Specific surface area m²/g | Particle length mm | Ratio of specific surface area to particle length m²/mm |
|---|---|---|---|---|---|---|---|---|---|
| 1 | 60A1 | Butterfly shape Average diameter of 1.8 mm | 0.38 | 0.21 | 1.81 | 0.55 | 560 | 135 | 4.15 |

TABLE 1-continued

Properties of solid acid catalysts obtained in Examples 1-9 and Comparative Examples 1-3

| Ex. No. | Catalyst No. | Particle shape of solid acid catalyst | Macropore specific volume ml/g | Specific length of particles mm | Ratio of macropore specific volume to specific length of particles ml/(g · mm) | Total pore specific volume ml/g | Specific surface area m²/g | Particle length mm | Ratio of specific surface area to particle length m²/mm |
|---|---|---|---|---|---|---|---|---|---|
| 2 | 80A1 | Butterfly shape Average diameter of 1.8 mm | 0.32 | 0.21 | 1.5 | 0.48 | 590 | 147 | 4.01 |
| 3 | 95A1 | Butterfly shape Average diameter of 1.8 mm | 0.3 | 0.21 | 1.43 | 0.47 | 651 | 150 | 4.34 |
| 4 | 60A2 | Butterfly shape Average diameter of 1.8 mm | 0.39 | 0.21 | 1.86 | 0.56 | 550 | 138 | 3.99 |
| 5 | 80A2 | Butterfly shape Average diameter of 1.8 mm | 0.35 | 0.21 | 1.7 | 0.51 | 580 | 137 | 4.09 |
| 6 | 95A2 | Butterfly shape Average diameter of 1.8 mm | 0.3 | 0.21 | 1.43 | 0.48 | 648 | 145 | 4.47 |
| 7 | 60A3 | Butterfly shape Average diameter of 1.8 mm | 0.4 | 0.21 | 1.9 | 0.58 | 548 | 139 | 3.94 |
| 8 | 80A3 | Cylindrical shape Average diameter of 1.3 mm | 0.32 | 0.29 | 1.1 | 0.45 | 600 | 135 | 4.44 |
| 9 | 95A3 | Butterfly shape Average diameter of 1.8 mm | 0.3 | 0.21 | 1.43 | 0.47 | 639 | 148 | 4.32 |
| Comp. Ex. 1 | 60A | Butterfly shape Average diameter of 1.8 mm | 0.40 | 0.21 | 1.9 | 0.57 | 540 | 170 | 3.18 |
| Comp. Ex. 2 | 80A | Butterfly shape Average diameter of 1.8 mm | 0.37 | 0.21 | 1.7 | 0.53 | 570 | 175 | 3.26 |
| Comp. Ex. 3 | 95A | Butterfly shape Average diameter of 1.8 mm | 0.32 | 0.21 | 1.52 | 0.5 | 638 | 135 | 4.73 |

The solid acid catalyst 80A2 and the comparative solid acid catalyst 80A were characterized using SEM and EDX mapping, and the morphology and elemental distribution results are shown in FIG. 1.

As can be seen from FIG. 1, the distribution of silicon and aluminum elements in the solid acid catalyst 80A2 is more uniform, which indicates that the particle size distribution of the Y molecular sieve and the $Al_2O_3$ is more uniform and the degree of acid site dispersion is higher after the liquid phase mixing.

Examples 10 to 18

These examples illustrate the preparation of an alkylation catalyst according to the present application.

The alkylation catalysts of Examples 10-18 were obtained by loading a metal having a hydrogenation capability onto the solid acid catalysts of Examples 1-9, respectively. The solid acid catalysts 60A1, 80A1, 95A1, 60A2, 80A2, 95A2, 60A3, 80A3 and 95A3 obtained in Examples 1 to 9 are respectively added into an impregnation solution containing hydrogenation metal Pt (using $H_2PtCl_6.6H_2O$ as a precursor) under vacuum with a liquid-to-solid ratio of 2:1. After the addition, the impregnation was carried out for 3 hours under normal pressure, and then the impregnation vessel was evacuated at a temperature of not higher than 80° C. to remove the moisture in the catalyst by evaporation until the weight of the catalyst was 1.2 to 1.5 times of that of the initial solid acid catalyst. After the evaporation, the catalyst was taken out, dried at 110° C. for 4 hours, and calcined at 500° C. for 2 hours under air atmosphere to obtain the target alkylation catalyst.

The measured data showed that the alkylation catalysts obtained were substantially the same as the solid acid catalysts used in the properties shown in Table 1.

The alkylation catalysts obtained are designated as C1, C2, C3, C4, C5, C6, C7, C8 and C9, respectively, all of which have a Pt content of 0.25 wt %.

Examples 19 to 22

These examples illustrate the preparation of an alkylation catalyst according to the present application.

The alkylation catalysts of Examples 19-22 were obtained by loading a metal having a hydrogenation capability onto the solid acid catalyst 80A2 of Example 5. The preparation was carried out as described in Example 14, and alkylation catalysts with different contents of the hydrogenation metal were obtained, which are designated as C10-$C_{13}$, respectively. The Pt contents of the alkylation catalysts $C_{10}$-$C_{13}$ were 0.1 wt %, 0.5 wt %, 0.7 wt %, and 0.9 wt %, respectively.

Example 23

This example illustrates the preparation of an alkylation catalyst according to the present application.

The alkylation catalyst of Example 23 was obtained by loading a metal having a hydrogenation capability onto the solid acid catalyst 80A2 of Example 5. The preparation was carried out as described in Example 14, except that the hydrogenation metal was Pd (using palladium nitrate as a precursor), the Pd content was 0.5 wt % and the catalyst was designated as C14.

Example 24

This example illustrates the preparation of an alkylation catalyst according to the present application.

The alkylation catalyst of Example 24 was obtained by loading a metal having a hydrogenation capability onto the solid acid catalyst 80A2 of Example 5. The preparation was carried out as described in Example 14, except that the hydrogenation metal was Ru (using ruthenium chloride as a precursor), the Ru content was 0.5 wt % and the catalyst was designated as C15.

Example 25

This example illustrates the preparation of an alkylation catalyst according to the present application.

The alkylation catalyst of Example 25 was obtained by loading a metal having a hydrogenation capability onto the solid acid catalyst 80A2 of Example 5. The preparation was carried out as described in Example 14, except that the hydrogenation metal was Mn (using manganese nitrate as a precursor), the Mn content was 3.5 wt % and the catalyst was designated as C16.

Example 26

This example illustrates the preparation of an alkylation catalyst according to the present application.

The alkylation catalyst of Example 26 was obtained by loading a metal having a hydrogenation capability onto the solid acid catalyst 80A2 of Example 5. The preparation was carried out as described in Example 14, except that the hydrogenation metal was Ni (using nickel nitrate as a precursor), the Ni content was 3.5 wt % and the catalyst was designated as C17.

Examples 27 to 35

These examples illustrate the use of alkylation catalysts according to the present application in alkylation reactions.

The alkylation reaction of isobutane with a mixed butene was carried out in Examples 27-35 using alkylation catalysts C1, C2, C3, C4, C5, C6, C7, C8, C9, respectively. The mixed butene comprised 25% 1-butene, 37.5% trans-2-butene, 35% cis-2-butene, and 2.5% isobutene, by volume.

The reaction conditions were as follows: a molar ratio of isobutane to the mixed butene of 200, a reaction temperature of 75° C., a reaction pressure of 3 MPa, and a total feed rate of 100 ml/($g_{cat}$·h).

The results of the alkylation reaction are shown in Table 2.

Example 36

This example illustrates the use of the alkylation catalyst according to the present application in alkylation reactions.

The alkylation reaction of isobutane with the mixed butene was carried out in Example 36 using the alkylation catalyst C5.

The reaction conditions were as follows: a molar ratio of isobutane to the mixed butene of 20, a reaction temperature of 40° C., a reaction pressure of 2 MPa, and a total feed rate of 10 ml/($g_{cat}$·h).

The results of the alkylation reaction are shown in Table 2.

Example 37

This example illustrates the use of the alkylation catalyst according to the present application in alkylation reactions.

The alkylation reaction of isobutane with the mixed butene was carried out in Example 37 using the alkylation catalyst C5.

The reaction conditions were as follows: a molar ratio of isobutane to the mixed butene of 500, a reaction temperature of 75° C., a reaction pressure of 3 MPa, and a total feed rate of 1000 ml/($g_{cat}$·h).

The results of the alkylation reaction are shown in Table 2.

Example 38

This example illustrates the use of the alkylation catalyst according to the present application in alkylation reactions.

The alkylation reaction of isobutane with the mixed butene was carried out in Example 38 using the alkylation catalyst C5.

The reaction conditions were as follows: a molar ratio of isobutane to the mixed butene of 1000, a reaction temperature of 100° C., a reaction pressure of 5 MPa, and a total feed rate of 3000 ml/($g_{cat}$·h).

The results of the alkylation reaction are shown in Table 2.

Examples 39-46

This example illustrates the use of the alkylation catalyst according to the present application in alkylation reactions.

The alkylation reaction of isobutane with the mixed butene was carried out in Examples 39-46 using alkylation catalysts C10, C11, C12, C13, C14, C15, C16 and C17, respectively, under the same alkylation conditions as in Example 27.

The results of the alkylation reaction are shown in Table 2.

Comparative Examples 4 to 6

Comparative Examples 4-6 illustrate the preparation of alkylation catalysts not according to the present application, and effects thereof in alkylation reactions.

Comparative alkylation catalysts of Comparative Examples 4 to 6 were obtained by loading hydrogenation metal Pt on comparative solid acid catalysts 60A, 80A and 95A obtained in Comparative Examples 1 to 3, respectively, and the preparation was carried out as described in Example 14 with a Pt content of 0.25 wt %, and the catalysts were designated as DB1, DB2 and DB3, respectively.

The resulting comparative alkylation catalysts were used for the alkylation of isobutane with the mixed butene under the same alkylation conditions as in Example 31.

The results of the alkylation reaction are shown in Table 2.

Comparative Example 7

This comparative example illustrates the preparation of an alkylation catalyst not according to the present application, and effects thereof in alkylation reactions.

The comparative alkylation catalyst of this comparative example had a same composition as the alkylation catalyst C4 of Example 13 (having a Pt content of 0.25 wt %), and was prepared in a similar manner, except that: the shaped solid acid catalyst had a cylindrical shape; a ratio of macropore specific volume to specific length of catalyst particles of 0.82 ml/(g·mm) (with the macropore specific volume of the catalyst being 0.4 ml/g, the specific length of catalyst particles being 0.49 mm, and the average diameter being 2.2 mm), a total pore specific volume of 0.5 ml/g, a specific surface area of 545 m$^2$/g, a length of catalyst particles of 140 mm, a ratio of specific surface area to length of catalyst particles of 3.89 m$^2$/mm, and the catalyst obtained was designated as DB4.

The resulting comparative alkylation catalyst was used for the alkylation of isobutane with the mixed butene under the same alkylation conditions as in Example 31.

The results of the alkylation reaction are shown in Table 2.

Comparative Example 8

This comparative example illustrates the preparation of an alkylation catalyst not according to the present application, and effects thereof in alkylation reactions.

The comparative alkylation catalyst of this comparative example had a same composition as the alkylation catalyst C4 of Example 13 (having a Pt content of 0.25 wt %), and was prepared in a similar manner, except that: the shaped solid acid catalyst had a spherical shape; a ratio of macropore specific volume to specific length of catalyst particles of 0.51 ml/(g·mm) (with the macropore specific volume of the catalyst being 0.42 ml/g, the specific length of catalyst particles being 0.83 mm, and the average diameter being 5.0 mm), a total pore specific volume of 0.55 ml/g, a specific surface area of 555 m$^2$/g, a length of catalyst particles of 145 mm, a ratio of specific surface area to length of catalyst particles of 3.83 m$^2$/mm, and the catalyst obtained was designated as DB5.

The resulting comparative alkylation catalyst was used for the alkylation reaction of isobutane with the mixed butene under the same alkylation conditions as in Example 31.

The results of the alkylation reaction are shown in Table 2.

Comparative Example 9

This comparative example illustrates the preparation of an alkylation catalyst not according to the present application, and effects thereof in alkylation reactions.

The comparative alkylation catalyst of this comparative example had a same composition as the comparative alkylation catalyst DB2 of Comparative Example 5 (having a Pt content of 0.25 wt %), and was prepared in a similar manner, except that: the shaped solid acid catalyst had a cylindrical shape; a ratio of macropore specific volume to specific length of catalyst particles of 1.90 ml/(g·mm) (with the macropore specific volume of the catalyst being 0.40 ml/g, the specific length of catalyst particles being 0.21 mm, and the average diameter being 1.8 mm), a total pore specific volume of 0.48 ml/g, a specific surface area of 570 m$^2$/g, a length of catalyst particles of 175 mm, a ratio of specific surface area to length of catalyst particles of 3.26 m$^2$/mm, and the catalyst obtained was designated as DB6.

The resulting comparative alkylation catalyst was used for the alkylation reaction of isobutane with the mixed butene under the same alkylation conditions as in Example 31.

The results of the alkylation reaction are shown in Table 2.

TABLE 2

Results of Examples 27-46 and Comparative Examples 4-9

| Examples | Alkylation catalyst | Catalyst service | TMP | C$_9$+ |
|---|---|---|---|---|
| 27 | C1, Pt 0.25 wt % | 60 | 65 | 7.8 |
| 28 | C2, Pt 0.25 wt % | 75 | 74.5 | 2.8 |
| 29 | C3, Pt 0.25 wt % | 74 | 73.8 | 2.5 |
| 30 | C4, Pt 0.25 wt % | 58 | 64.5 | 7.9 |
| 31 | C5, Pt 0.25 wt % | 72 | 73.6 | 3.7 |
| 32 | C6, Pt 0.25 wt % | 71 | 73.5 | 2.6 |
| 33 | C7, Pt 0.25 wt % | 56 | 64 | 8.0 |
| 34 | C8, Pt 0.25 wt % | 70 | 72.8 | 4.5 |
| 35 | C9, Pt 0.25 wt % | 69 | 72.7 | 2.7 |
| 36 | C5, Pt 0.25 wt % | 22 | 43.0 | 11.5 |
| 37 | C5, Pt 0.25 wt % | 33 | 77.0 | 2.3 |
| 38 | C5, Pt 0.25 wt % | 17 | 75.2 | 1.8 |
| 39 | C10, Pt 0.1 wt % | 75 | 74.0 | 3.6 |
| 40 | C11, Pt 0.5 wt % | 71 | 73.5 | 3.3 |
| 41 | C12, Pt 0.7 wt % | 70 | 73.2 | 3.2 |
| 42 | C13, Pt 0.9 wt % | 70 | 73.4 | 3.2 |
| 43 | C14, Pd 0.5 wt % | 71 | 73.4 | 3.2 |
| 44 | C15, Ru 0.5 wt % | 71 | 73.3 | 3.2 |
| 45 | C16, Mn 3.5 wt % | 70 | 73.2 | 3.1 |
| 46 | C17, Ni 3.5 wt % | 71 | 73.5 | 3.3 |
| Comp. Ex. 4 | DB1, Pt 0.25 wt % | 45 | 58.5 | 9.9 |
| Comp. Ex. 5 | DB2, Pt 0.25 wt % | 63 | 66.8 | 5.1 |
| Comp. Ex. 6 | DB3, Pt 0.25 wt % | 65 | 68.5 | 4.3 |
| Comp. Ex. 7 | DB4, Pt 0.25 wt % | 38 | 71.8 | 7.9 |
| Comp. Ex. 8 | DB5, Pt 0.25 wt % | 32 | 68.5 | 8.6 |
| Comp. Ex. 9 | DB6, Pt 0.25 wt % | 40 | 65.2 | 10.3 |

As can be seen from Table 2, where the composition of the catalysts are substantially the same, the catalysts having a ratio of macro specific volume to specific length of catalyst particles and a ratio of specific surface area to length of catalyst particles within the scope of the present application have higher degree of acid site dispersion, more reasonable pore structure distribution, and better diffusion performance for reaction product, and thus show a higher TMP selectivity, a lower $C_{9+}$ selectivity, and a longer catalyst service life in the alkylation of isobutane with the mixed butene. In contrast, the comparative alkylation catalysts having a ratio of macropore specific volume to specific length of catalyst particle and/or a ratio of specific surface area to length of catalyst particles falling outside the scope of the present application show a shorter catalyst service life and a higher $C_{9+}$ selectivity.

Example 47

This example illustrates the preparation and use of an alkylation catalyst according to the present application using a β molecular sieve as the solid acid component.

The alkylation catalyst of this example was prepared as described in Examples 5 and 14, except that the Y molecular sieve was replaced with a β molecular sieve (Catalyst Branch of Sinopec, having a relative crystallinity of 89%).

The resulting alkylation catalyst was designated as C18, with the hydrogenation metal being Pt and the content thereof being 0.25 wt %.

The resulting alkylation catalyst was used for the alkylation reaction of isobutane with the mixed butene under the same alkylation conditions as in Example 27.

The properties of the catalyst obtained are shown in Table 3, and the results of the alkylation reaction are shown in Table 4.

Example 48

This example illustrates the preparation and use of an alkylation catalyst according to the present application using an MCM-22 molecular sieve as the solid acid component.

The alkylation catalyst of this example was prepared as described in Examples 5 and 14, except that the Y molecular sieve was replaced with an MCM-22 molecular sieve (Nankai Catalyst Plant, having a crystallinity of 86%).

The resulting alkylation catalyst was designated as C19, with the hydrogenation metal being Pt and the content thereof being 0.25 wt %.

The resulting alkylation catalyst was used for the alkylation reaction of isobutane with the mixed butene under the same alkylation conditions as in Example 27.

The properties of the catalyst obtained are shown in Table 3, and the results of the alkylation reaction are shown in Table 4.

Example 49

This example illustrates the preparation and use of an alkylation catalyst according to the present application using an MOR molecular sieve as the solid acid component.

The alkylation catalyst of this example was prepared as described in Examples 5 and 14, except that the Y molecular sieve was replaced with an MOR molecular sieve (Catalyst Branch of Sinopec, having a relative crystallinity of 117.6%).

The resulting alkylation catalyst was designated as C20, with the hydrogenation metal being Pt and the content thereof being 0.25 wt %.

The resulting alkylation catalyst was used for the alkylation reaction of isobutane with the mixed butene under the same alkylation conditions as in Example 27.

The properties of the catalyst obtained are shown in Table 3, and the results of the alkylation reaction are shown in Table 4.

Comparative Example 10

This comparative example illustrates the preparation of an alkylation catalyst not according to the present application using a β molecular sieve as the solid acid component, and effects thereof in alkylation reactions.

Comparative alkylation catalyst of this comparative example was prepared as described in Comparative Example 2 and Comparative Example 5, except that the Y molecular sieve was replaced with a β molecular sieve (Catalyst Branch of Sinopec, having a relative crystallinity of 89%).

The resulting comparative alkylation catalyst was designated as DB10 with the hydrogenation metal being Pt and the content thereof being 0.25 wt %.

The resulting comparative alkylation catalyst was used for the alkylation reaction of isobutane with the mixed butene under the same alkylation conditions as in Example 27.

The properties of the catalyst obtained are shown in Table 3, and the results of the alkylation reaction are shown in Table 4.

Comparative Example 11

This comparative example illustrates the preparation of an alkylation catalyst not according to the present application using a β molecular sieve as the solid acid component, and effects thereof in alkylation reactions.

The comparative alkylation catalyst of this comparative example had a same composition as the alkylation catalyst C18 of Example 47 (having a Pt content of 0.25 wt %), and was prepared in a similar manner, except that: the shaped solid acid catalyst had a spherical shape; a ratio of macropore specific volume to specific length of catalyst particles of 0.52 ml/(g·mm) (with the macropore specific volume of the catalyst being 0.43 ml/g, the specific length of catalyst particles being 0.83 mm, and the average diameter being 5.0 mm), a total pore specific volume of 0.63 ml/g, a specific surface area of 545 m²/g, a length of catalyst particles of 150 mm, a ratio of specific surface area to length of catalyst particles of 3.83 m²/mm, and the catalyst obtained was designated as DB11.

The resulting comparative alkylation catalyst was used for the alkylation reaction of isobutane with the mixed butene under the same alkylation conditions as in Example 27.

The properties of the catalyst obtained are shown in Table 3, and the results of the alkylation reaction are shown in Table 4.

TABLE 3

Properties of catalysts obtained in Examples 47-49 and Comparative Examples 10-11

| Ex. No. | Catalyst No. | Particle shape of solid acid catalyst | Macropore specific volume ml/g | Specific length of particles mm | Ratio of macropore specific volume to specific length of particles ml/(g·mm) | Total pore specific volume ml/g | Specific surface area m²/g | Particle length mm | Ratio of specific surface area to particle length m²/mm |
|---|---|---|---|---|---|---|---|---|---|
| 47 | C18 | Butterfly shape Average diameter of 1.8 mm | 0.41 | 0.21 | 1.7 | 0.68 | 547 | 143 | 3.83 |
| 48 | C19 | Butterfly shape Average diameter of 1.8 mm | 0.50 | 0.21 | 2.4 | 0.97 | 505 | 148 | 3.41 |
| 49 | C20 | Butterfly shape Average diameter of 1.8 mm | 0.31 | 0.21 | 1.5 | 0.46 | 525 | 125 | 4.20 |
| Comp. Ex. 10 | DB10 | Butterfly shape Average diameter of 1.8 mm | 0.40 | 0.21 | 1.9 | 0.65 | 550 | 170 | 3.24 |
| Comp. Ex. 11 | DB11 | Spherical shape Average diameter of 5 mm | 0.43 | 0.83 | 0.52 | 0.63 | 545 | 150 | 3.63 |

TABLE 4

Results of Examples 47-49 and Comparative Examples 10-11

| Examples | Alkylation catalyst | Catalyst service life/h | TMP selectivity/% | $C_9+$ selectivity/% |
|---|---|---|---|---|
| 47 | C18, β molecular sieve, Pt 0.25 wt % | 32 | 50.5 | 15.2 |
| 48 | C19, MCM-22 molecular sieve, Pt 0.25 wt % | 5 | 58 | 3.1 |
| 49 | C20, MOR molecular sieve, Pt 0.25 wt % | 4 | 82.6 | 5.8 |
| Comp. Ex. 10 | DB10, β molecular Sieve, Pt 0.25 wt % | 25 | 45.5 | 17.8 |
| Comp. Ex. 11 | DB11, β molecular Sieve, Pt 0.25 wt % | 19 | 40.5 | 19.8 |

As shown by the data listed in Table 4, the alkylation catalysts according to the present application using β molecular sieve, MCM-22 molecular sieve, and MOR molecular sieve as the solid acid component, although being slightly inferior in reaction performance to the alkylation catalysts according to the present application using Y molecular sieve as the solid acid component, still show significant improvements over alkylation catalysts not according to the present application having similar compositions.

The present application is illustrated in detail hereinabove with reference to preferred embodiments, but is not intended to be limited to those embodiments. Various modifications may be made following the inventive concept of the present application, and these modifications shall be within the scope of the present application.

It should be noted that the various technical features described in the above embodiments may be combined in any suitable manner without contradiction, and in order to avoid unnecessary repetition, various possible combinations are not described in the present application, but such combinations shall also be within the scope of the present application.

In addition, the various embodiments of the present application can be arbitrarily combined as long as the combination does not depart from the spirit of the present application, and such combined embodiments should be considered as the disclosure of the present application.

The invention claimed is:

1. A solid acid catalyst, having a macropore specific volume in a range of about 0.30-0.50 ml/g; a ratio of macropore specific volume to specific length of catalyst particles in a range of about 1.0-2.5 ml/(g·mm); and a ratio of specific surface area to length of catalyst particles in a range of about 3.40-4.50 m²/mm, wherein the macropore refers to pores having a diameter of greater than 50 nm.

2. The solid acid catalyst according to claim 1, wherein the solid acid catalyst further has one or more of the following characteristics:
   a specific length of catalyst particles in a range of about 0.15-0.4 mm;
   a total pore specific volume of at least about 0.40 ml/g; and
   a specific surface area of not less than about 500 m²/g.

3. The solid acid catalyst according to claim 1, wherein the solid acid catalyst comprises a solid acid component and a matrix material, and wherein, based on the total weight of the solid acid component and the matrix material, the solid acid catalyst comprises about 2-98 wt % of the solid acid component and about 2-98 wt % of the matrix material.

4. The solid acid catalyst according to claim 3, wherein the solid acid component comprises a molecular sieve.

5. The solid acid catalyst according to claim 4, wherein the solid acid component comprises a Y molecular sieve having a lattice constant in a range of about 2.430-2.470 nm.

6. The solid acid catalyst according to claim 3, wherein the solid acid component comprises one or more selected from the group consisting of heteropolyacids, silica-alumina, sulfated oxides, chlorided alumina, and clays.

7. The solid acid catalyst according to claim 3, wherein the matrix material is an alumina matrix material.

8. The solid acid catalyst according to claim 1, wherein the macropore specific volume is in a range of about 0.30-0.40 ml/g, the ratio of macropore specific volume to specific length of catalyst particles is in a range of about 1.1-1.8 ml/(g·mm).

9. A method for preparing the solid acid catalyst according to claim 1, comprising the steps of:
i) providing a slurry comprising a solid acid component;
ii) mixing the slurry comprising the solid acid component with an alumina sol and drying the resulting mixture; and
iii) mixing the dried mixture with an extrusion aid and a peptizing agent and shaping, wherein the alumina sol has a particle size in a range of about 20-400 nm.

10. The method according to claim 9, wherein the alumina sol is used in an amount of about 2-98 wt % calculated as alumina and based on the total weight of the solid acid component and the alumina sol.

11. The method according to claim 9, wherein the extrusion aid is at least one selected from the group consisting of sesbania powder, oxalic acid, tartaric acid and citric acid; and the peptizing agent is at least one selected from the group consisting of nitric acid, hydrochloric acid, acetic acid, formic acid, citric acid, and trichloroacetic acid.

12. The method according to claim 9, wherein the alumina sol has a particle size in a range of about 20-400 nm, and the solid acid component comprises one or more selected from the group consisting of molecular sieves, heteropolyacids, silica-alumina, sulphated oxides, chlorided alumina, and clays.

13. A solid acid-based alkylation catalyst, comprising a metal component having a hydrogenation capability, wherein the metal component is present in an amount of about 0.01-10 wt %, calculated as metal and based on the weight of the alkylation catalyst, and the alkylation catalyst has a macropore specific volume in a range of about 0.30-0.50 ml/g; a ratio of macropore specific volume to specific length of catalyst particles in a range of about 1.0-2.5 ml/(g·mm); and a ratio of specific surface area to length of catalyst particles in a range of about 3.40-4.50 m$^2$/mm, wherein the macropore refers to pores having a diameter of greater than 50 nm.

14. The alkylation catalyst according to claim 13, wherein the metal having a hydrogenation capability is a Group VIII metal.

15. The alkylation catalyst according to claim 13, wherein the metal component having a hydrogenation capability is supported on a solid acid catalyst, Wherein the solid acid catalyst has a macropore specific volume in a range of about 0.30-0.50 ml/g; a ratio of macropore specific volume to specific length of catalyst particles in a range of about 1.0-2.5 ml/(g·mm); and a ratio of specific surface area to length of catalyst particles in a range of about 3.40-4.50 m$^2$/mm, wherein the macropore refers to pores having a diameter of greater than 50 nm.

16. A method for preparing the alkylation catalyst according to claim 13, comprising the steps of:
i) providing a shaped solid acid catalyst,
ii) loading a metal having a hydrogenation capability onto the solid acid catalyst to obtain a catalyst precursor, and
iii) drying and calcining the catalyst precursor obtained in step ii) to obtain the alkylation catalyst,
wherein the solid acid catalyst has a macropore specific volume in a range of about 0.30-0.50 ml/g, a ratio of macropore specific volume to specific length of catalyst particles in a range of about 1.0-2.5 ml/(g·mm), and a ratio of specific surface area to length of catalyst particles in a range of about 3.40-4.50 m$^2$/mm, wherein the macropore refers to pores having a diameter greater than 50 nm.

17. A method for preparing the alkylation catalyst according to claim 13, comprising the steps of:
i) providing a slurry comprising a solid acid component;
ii) mixing the slurry comprising the solid acid component with an alumina sol and a precursor of a metal having a hydrogenation capability and drying the resulting mixture; and
iii) mixing the dried mixture with an extrusion aid and a peptizing agent and shaping,
wherein the alumina sol has a particle size in a range of about 20-400 nm.

18. An alkylation process, comprising a step of subjecting an isoparaffin to an alkylation reaction with an olefin in the presence of the solid acid catalyst according to claim 1.

19. The process according to claim 18, wherein the alkylation reaction is carried out under the following conditions:
a temperature of about 30-100° C., a pressure of about 1.5-5.0 MPa, a feed rate of about 10-3000 ml/($g_{cat}$·h), and a molar ratio of isoparaffin to olefin of about 6-1000.

20. An alkylation process, comprising a step of subjecting an isoparaffin to an alkylation reaction with an olefin in the presence of the alkylation catalyst according to claim 13.

21. The process according to claim 20, wherein the alkylation reaction is carried out under the following conditions:
a temperature of about 30-100° C., a pressure of about 1.5-5.0 MPa, a feed rate of about 10-3000 ml/($g_{cat}$·h), and a molar ratio of isoparaffin to olefin of about 6-1000.

\* \* \* \* \*